United States Patent [19]

Blitshteyn et al.

[11] Patent Number: 4,774,472

[45] Date of Patent: Sep. 27, 1988

[54] APPARATUS FOR METHOD TO TEST EFFICIENCY OF AIR IONIZERS AND METHOD FOR DETERMINING ABILITY OF AN AIR IONIZER TO SUSTAIN A POTENTIAL DIFFERENCE BETWEEN AN ISOLATED OBJECT AND A REFERENCE POTENTIAL

[75] Inventors: Mark Blitshteyn, Edison, N.J.; William S. Wright, Green Lane, Pa.

[73] Assignee: The Simco Company, Inc., Hatfield, Pa.

[21] Appl. No.: 843,140

[22] Filed: Mar. 24, 1986

[51] Int. Cl.$^4$ ............................................. G01N 27/70
[52] U.S. Cl. ..................................... 324/464; 324/459; 361/213
[58] Field of Search ................... 250/287; 340/629; 324/457, 72, 459, 464, 72.5, 458; 361/213, 220, 231, 222

[56] References Cited

U.S. PATENT DOCUMENTS 3,728,615  4/1973  Hill et al. ............................. 324/464
4,542,434  9/1985  Gehlke et al. ....................... 361/213

OTHER PUBLICATIONS

Antonevich, John N. and Mark Blitshteyn, "Measuring Effectiveness of Air Ionizer, "Electrical Overstress-/Electrostatic Discharge Symposium Proceedings, 1983.

Testone, Anthony Q., Static Electricity in the Electronics Industry (1980) pp. 50-53.

Primary Examiner—Reinhard J. Eisenzopf
Assistant Examiner—Anthony L. Miele
Attorney, Agent, or Firm—Barnes & Thornburg

[57] ABSTRACT

A method and apparatus for determining ion flow imbalance. High-magnitude positive and negative potential sources, each having a high-magnitude potential output terminal, are provided. Two electrodes are adapted for positioning adjacent the location of ions, the electrodes having areas for exposure to the ions. A supply of operating potential is provided for the high-magnitude potential sources. The operating potential supply is switched to supply operating potential alternately between the high-magnitude potential sources. Neutral terminals are provided on each of the high-magnitude potential sources and the current flows from the neutral terminals of the high-magnitude potential sources to reference potential are sensed to determine the current flows to the electrodes.

27 Claims, 3 Drawing Sheets

APPARATUS FOR METHOD TO TEST EFFICIENCY OF AIR IONIZERS AND METHOD FOR DETERMINING ABILITY OF AN AIR IONIZER TO SUSTAIN A POTENTIAL DIFFERENCE BETWEEN AN ISOLATED OBJECT AND A REFERENCE POTENTIAL

This invention relates to an ion density meter. Such instruments are particularly useful, for example, to determine the ion generating efficiency of air ionizing equipment. Measuring the effectiveness of air ionizers has been proposed in the past. There are, for example, the proposals outlined at Electrical Overstress/Electrostatic Discharge Symposium Proceedings 1983 pp. 1-11.

According to the present invention, an ion current measuring instrument comprises high-magnitude positive and negative potential sources. Each of the high-magnitude potential sources has a high-magnitude potential output terminal. Means are provided for selectively energizing one or the other of the high-magnitude potential sources. Two electrodes are provided for positioning adjacent the source of ions, the electrodes having areas for exposure to the ions. Means are provided for coupling the high-magnitude potential output terminal of each of the high-magnitude potential sources to a respective one of the electrodes.

According to an illustrative embodiment of the invention, the means for selectively energizing one or the other of the high-magnitude potential sources comprises a supply for providing operating potential. Each of the high-magnitude potential sources has an operating potential input terminal. A switch has a position in which operating potential is coupled to the operating potential terminal of the high-magnitude positive potential supply and a position in which operating potenial is coupled to the operating potential terminal of the high-magnitude negative potential supply. Illustratively, the switch also has a position in which operating potential is supplied to neither high-magnitude potential supply.

Additionally, according to the illustrative embodiment, the operating potential supply comprises a voltage regulator.

Further according to the illustrative embodiment, each of the high-magnitude potential sources further comprises a neutral terminal. The instrument further comprises means for sensing current flows to reference potential from the high-magnitude potential sources. Ions impacting on the electrode coupled to the energized high-magnitude potential supply cause current flow through that high-magnitude supply's neutral terminal to reference potential. The current sensing means senses this ion current flow to reference potential and provides an indication of it.

Additionally according to the illustrative embodiment, a shield surrounds, and is closely spaced to, the electrodes. Means are provided for coupling the shield to the neutral terminals of both high-magnitude potential sources.

According to the illustrative embodiment, the means for sensing current flows from the high-magnitude potential sources to reference potential comprises a resistor, means for coupling the resistor between the neutral terminals of both high-magnitude potential sources and reference potential, a voltmeter, and means for coupling the voltmeter in parallel with the resistor. The voltmeter reading provides an indication of the ion current.

Illustratively, according to this aspect of the invention, the instrument further comprises a circuit for delaying the display by the voltmeter of any voltage across the resistor.

According to the illustrative embodiment, the delay circuit comprises a relay including an energizing coil and a switch for energization by the coil, means for coupling the relay switch in circuit with the resistor, means for timing an interval after energization of the instrument, and means for coupling the timing means to the relay coil. Timing of the interval causes a change in the current flowing in the relay coil, causing the relay switch to change state so that the resistor can sense the ion current flow.

Illustratively, the relay switch is open when no current flows in the relay coil, and the timing means comprises a Schmitt trigger.

Further according to the invention, the electrodes comprise plates having substantially equal areas, the plates together comprising a rectangular array, with each plate having an irregular edge. The irregular edges of the plates are complementarily configured for close spacing of the irregular edges from each other.

According to the illustrative embodiment, the irregular edges comprise multiple, finger-like protrusions. The protrusions forming the irregular edge of one plate are interleaved with the protrusions forming the irregular edge of the other plate. The plates thus define between their irregular edges a serpentine space.

According to the another aspect of the invention, the method for measuring the ion flow imbalance of an ionizer comprises the steps of providing high magnitude positive and negative potential supplies, the magnitudes of which are independently selectively variable, and providing two electrodes for positioning adjacent the flow of ions from the ionizer. The electrodes have areas for exposure to the ions. The method further comprises the steps of alternately energizing the electrodes from respective ones of the high magnitude potential supplies, alternately sensing ion flows to the respective electrodes, independently varying the magnitudes of the potentials supplied from the positive and negative supplies to their respective electrodes until the ion flows to the two electrodes are substantially equal, and comparing the magnitudes of the potentials.

According to an illustrative embodiment, the step of measuring the ion flow imbalance of an ionizer comprises the step of providing two plate-like electrodes having substantially equal areas. The step of alternately sensing ion current flows to the respective electrodes comprises the step of exposing the substantially equal areas of the two electrodes to the ions. The step of alternately energizing the electrodes from respective ones of the high magnitude potential supplies comprises the step of alternately energizing the supplies.

According to yet another aspect of the invention, a method for measuring the ion flow imbalance of an ionizer comprises the steps of providing high magnitude positive and negative potential supplies and providing two electrodes, the geometries of which are independently selectively variable, for positioning adjacent the flow of ions from the ionizer. The electrodes have areas for exposure to the ions. The method further comprises the steps of alternately energizing the electrodes from respective ones of the supplies, alternately sensing ion flow to the respective electrodes, independently varying the geometries of the electrodes until the ion flows to the two electrodes are equal, and comparing the geometries of the electrodes.

According to an illustrative embodiment, the step of providing two electrodes, the geometries of which are independently selectively variable comprises the step of providing more than two plate-like electrodes having different predetermined areas. The step of independently varying the geometries of the electrodes comprises the step of substituting an electrode having a first predetermined area for another electrode having a second and different predetermined area.

Additionally according to the invention, the step of providing high magnitude positive and negative potential supplies comprises the step of providing high magnitude positive and negative potential supplies, the magnitudes of which are independently selectively variable.

According to another aspect of the invention, a method for determining ion flow imbalance comprises the steps of providing high-magnitude positive and negative potential sources, each having a high-magnitude potential output terminal, providing two electrodes for positioning adjacent the location of ions, the electrodes having areas for exposure to the ions, alternately energizing one or the other of the two electrodes from respective high-magnitude potential sources and sensing the current flows to the electrodes as they are alternately energized.

Additionally, according to this aspect of the invention, the step of alternately energizing one or the other of the two electrodes from respective high-magnitude potential sources comprises the steps of providing a supply of operating potential for the high-magnitude potential sources, and switching the supply of operating potential alternately between the high-magnitude potential sources.

Further according to this aspect of the invention, the step of sensing the current flows to the electrodes as they are alternately energized comprises the steps of providing neutral terminals on each of the high-magnitude potential sources and sensing current flows from the neutral terminals of the high-magnitude potential sources to reference potential.

Additionally according to this aspect of the invention, the step of sensing current flows from the neutral terminals of the high-magnitude potential sources to reference potential comprises the steps of providing a resistor, coupling the resistor in series between the neutral terminals of the high-magnitude potential sources and reference potential, and sensing a voltage developed across the resistor by current flow through the resistor between the neutral terminals of the high-magnitude potential sources and reference potential.

According to yet another aspect of the invention, a method for determining the ability of an object subjected to an unbalanced stream of positive and negative ions to sustain a potential difference from a reference potential comprises the steps of establishing a functional relationship between an unbalance between positive and negative ion flows on the one hand and potential difference between the object and a reference potential on the other hand, measuring the positive ion current in the stream, measuring the negative ion current in the stream, determining the unbalance, and determining from the unbalance and the functional relationship the ability of the object to sustain the potential difference.

According to this aspect of the invention, the steps of measuring the positive ion current in the stream, measuring the negative ion current in the stream, and determining the unbalance together comprise the steps of providing high-magnitude positive and negative potential sources, each having a high-magnitude potential output terminal, providing two electrodes for positioning adjacent the stream of positive and negative ions, the electrodes having areas for exposure to the ions, alternately energizing the electrodes from respective high-magnitude potential sources, and alternately sensing the ion current flows to the electrodes.

Alternatively, according to this aspect of the invention, the steps of measuring the positive ion current in the stream, measuring the negative ion current in the stream, and determining the unbalance together comprise the steps of providing high-magnitude positive and negative potential sources, the magnitudes of which are independently selectively variable, each high-magnitude potential source having a high-magnitude potential output terminal, providing two electrodes for positioning adjacent the stream of positive and negative ions, the electrodes having areas for exposure to the ions, alternately energizing the electrodes from respective high-magnitude potential sources, independently varying the magnitudes of the potentials supplied from the positive and negative supplies to their respective electrodes until the ion flows to the two electrodes are substantially equal, and comparing the magnitudes of the potentials.

According to another alternative embodiment of this aspect of the invention, the steps of measuring the positive ion current in the stream, measuring the negative ion current in the stream, and determining the unbalance together comprise the steps of providing high-magnitude positive and negative potential supplies, providing two electrodes, the geometries of which are independently selectively variable for positioning adjacent the stream of positive and negative ions, the electrodes having areas for exposure to the ions, alternately energizing the electrodes from respective ones of the supplies, alternately sensing ion flow to the respective electrodes, independently varying the geometries of the electrodes until the ion flows to the two electrodes are equal, and comparing the geometries of the electrodes.

The invention may best be understood by referring to the following description and accompanying drawings which illustrate the invention. In the drawings.

Figure 1:
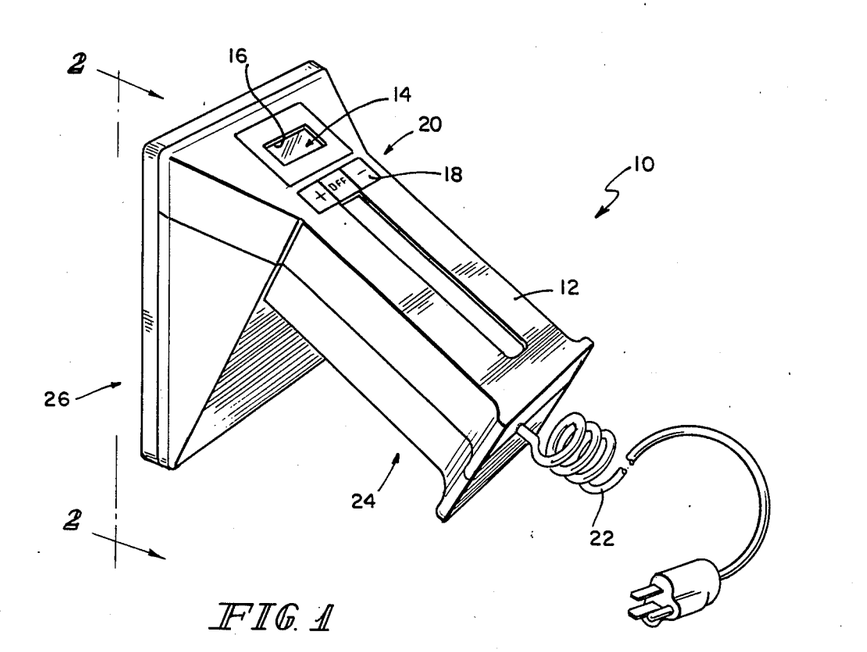
FIG. 1 is a perspective view of an ion current meter constructed according to the present invention.

Referring now particularly to FIG. 1, the ion current meter 10 of the present invention includes a case 12 which illustratively is a molded high-impact plastic case. A voltmeter 14 is mounted for visibility through a window 16 provided in the top of the case 12. An opening 18 is also provided in the top of the case 12 through which access in available to a three-position switch 20 including positions OFF, +and −. A power cord 22 extends from the end of a handle portion 24 of case 12.

Figure 2:
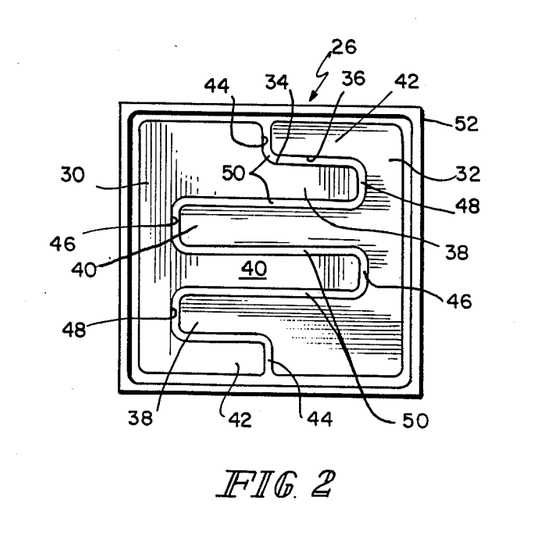
FIG. 2 is a sectional view taken generally along section lines 2—2 of FIG. 1.

The head portion 26 of case 12 includes a pair of plates 30, 32 (see FIG. 2). The case 12 is shaped so that the head 26, and particularly the plates 30, 32, can be conveniently placed in a region where ions are located. The plates 30, 32 have equal areas for exposure to the ions. The plates 30, 32 together comprise a rectangular array. Illustratively, the array is approximately square. Each plate 30, 32 has an irregular edge 34, 36, respectively, complementarily configured for close spacing of the irregular edges 34, 36 of plates 30, 32, respectively, from each other. Each of the irregular edges 34, 36 comprises multiple finger-like protrusions 38, 40, 42 with spaces 44, 46, 48 defined adjacent them to receive the finger-like protrusions 38, 40, 42 of the other plate 32, 30. This permits the protrusions 38, 40, 42 of the plates 30, 32 to be interleaved with the protrusions on the other plate 32, 30, defining between the irregular edges 34, 36 a serpentine non-conductive space 50. The reason why an elaborate configuration for plates 30, 32 is chosen is to provide that portions of both of plates 30, 32 are as evenly disposed across the measuring surface of the head 26 as possible. This is done to insure, to the greatest extent practicable, that the positive and negative plates 30, 32 both sample exactly the same cross-section of the ion current flow without being required to be moved. While particular configurations for plates 30, 32 have been illustrated, it is to be understood that a wide variety of different configurations which suitably address this requirement are possible.

It has been found in practice that the plates 30, 32 perform best when they are generated as a metallized film on a non-conductive surface such as TEFLON ® which retains high surface resistivity, in the range of $10^{11}$ ohms, even under high humidity conditions. Additionally, the insulative surface on which the plates 30, 32 are generated is provided with a conductive shield 52, such as a metallization, around its perimeter.

Figure 3:
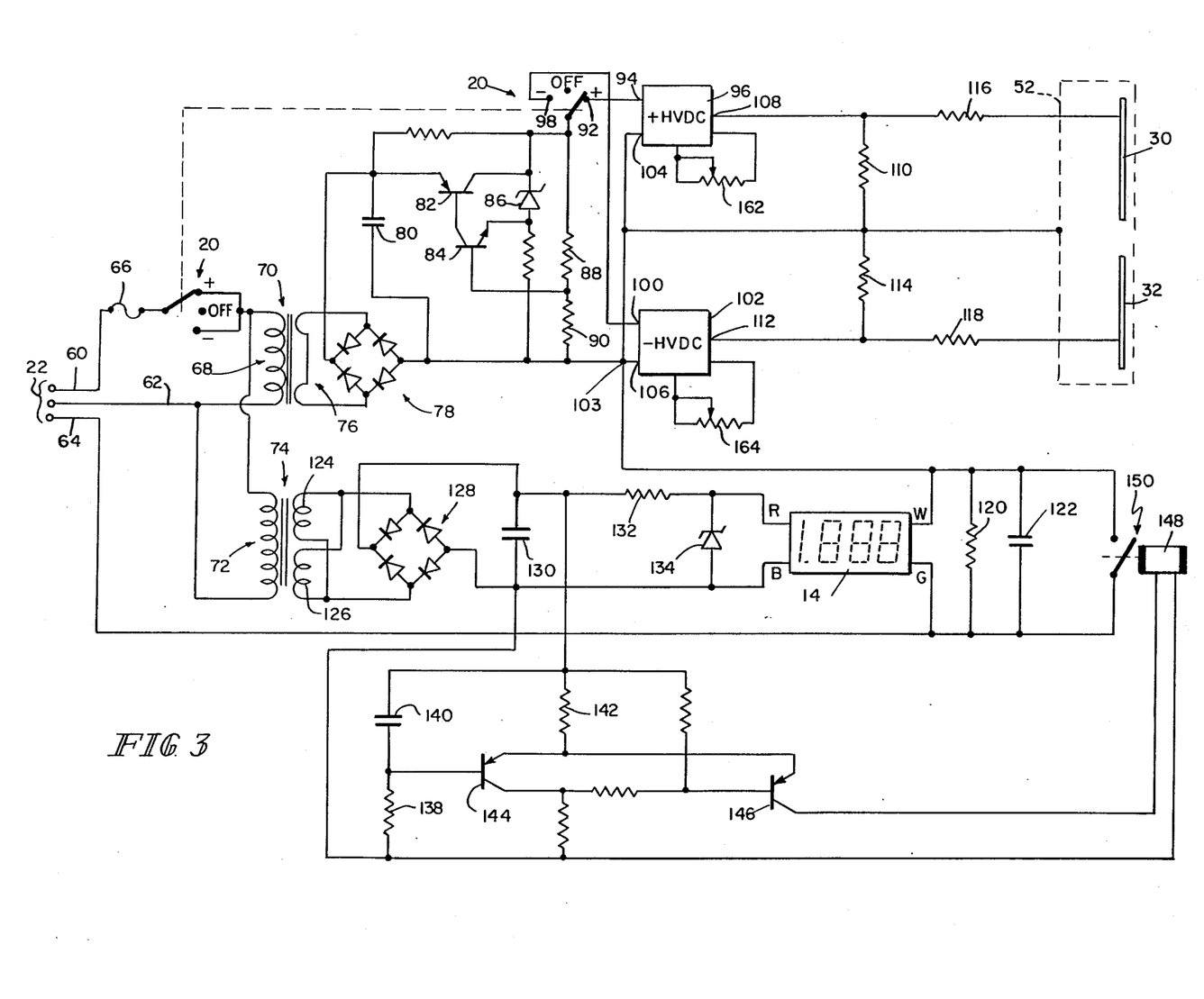
FIG. 3 is a schematic circuit diagram of the electric circuit of the ion current meter of FIGS. 1-2.

Turning now to FIG. 3, the power cord 22 includes conductors 60, 62, 64. A one-eighth ampere fuse 66, switch 20 and a primary winding 68 of a transformer 70 are coupled in series between conductors 60, 62. A primary winding 72 of a transformer 74 is coupled in parallel with primary winding 68. A secondary winding 76 of transformer 70 is coupled across a full-wave diode bridge 78 such as a 3N248 full-wave bridge. The joined anodes of two diodes in the bridge 78 are coupled to one terminal of a 10 uF, 250V capacitor 80. The other terminal of capacitor 80 is coupled to the joined cathodes of the remaining two diodes in bridge 78. A series voltage regulator for the voltage appearing across capacitor 80 includes a transistor 82 coupled in common-base configuration with its emitter coupled to the positive terminal of bridge 78. Transistor 82 illustratively is a type 2N6520 transistor. The base of transistor 82 is coupled to the collector of a transistor 84. The emitter of transistor 84 is coupled to an anode of a Zener diode 86. The cathode of Zener diode 86 is coupled to the collector of transistor 82. Transistor 84 illustratively is a type 2N6517. Diode 86 illustratively is a type 1N982B. A 15 K, one-half watt resistor is coupled across the emitter and collector of transistor 82. 120K resistor is coupled between the emitter of transistor 84 and the negative terminal of bridge 78. Two series resistors 88, 90 are coupled between the collector of transistor 82 and the negative terminal of bridge 78. The base of transistor 84 is coupled to the junction of resistors 88, 90. Resistor 88 illustratively is a 75K resistor. Resistor 90 illustratively is a 56K resistor.

Switch 20 includes a second set of terminals with three positions. The middle set of terminals of each part of switch 20 is the OFF position. The upper and right-most positions of the switch 20 movable contacts are the high-magnitude positive potential positions. The lower and left-most positions of the switch 20 movable contacts are the high-magnitude negative potential positions. Terminal 92 of switch 20 is coupled to the operating potential input terminal 94 of a +HVDC supply 96. Supply 96 illustratively is a type CS2073N2 supply, available from, for example, Collmer Semiconductor. Terminal 98 of switch 20 is coupled to the operating potential input terminal 100 of a −HVDC supply 102, such as a type CS2073N8 supply, also available from Collmer Semiconductor. The neutral terminals 104, 106 of supplies 96, 102, respectively, joined at 103 and are coupled to the negative terminal of bridge 78. The high-magnitude potential output terminal 108 of supply 96 is coupled through a 1G 15% resistor 110 to the common 103. The high-magnitude potential output terminal 112 of supply 102 is coupled through a 1G 15% resistor 114 to the common terminal 103. Terminal 108 is also coupled through an 80M resistor 116 to plate 30. Terminal 112 is also coupled through an 80M resistor 118 to plate 32. The shield 52 is coupled to the common terminal 103.

The common terminal 103 is coupled through a parallel RC circuit including a 100K, one-eighth watt, 1% resistor 120 and a 2.2 uF capacitor 122 to the ground conductor 64 of power cord 22. Transformer 74 includes parallel secondary windings 124, 126 coupled across a full-wave bridge rectifier 128 such as a type 3N247 bridge. A 100 uF, 35V capacitor 130 is coupled across the positive and negative terminals of bridge 128. A 1K resistor 132 and a Zener diode 134 in series are coupled across capacitor 130 with the resistor being coupled to the positive terminal of bridge 128 and the anode of the diode 134 being coupled to the negative terminal of bridge 128. The power supply leads of an LCD voltmeter 14 are coupled across diode 134, with the positive lead of the voltmeter 14 being coupled to the cathode of diode 134. Illustratively LCD voltmeter 14 is a type PCIM 176 voltmeter available, for example, from Semiconductor Circuits International. The measured voltage terminals of voltmeter 14 are coupled across resistor 120.

A delay circuit including a time-interval generating series RC combination of a 330K resistor 138 and a 10 uF capacitor 140 is coupled across the positive and negative terminals of bridge 128. One terminal of a 470 ohm resistor 142 is coupled to the positive terminal of bridge 128. The remaining terminal of resistor 142 is coupled to the emitters of two transistors 144, 146. Transistors 144, 146 illustratively are type MPS2907 transistors. The base of transistor 144 is coupled to the common terminal of resistor 138 and capacitor 140. The collector of transistor 144 is coupled through a 10K resistor to the negative terminal of bridge 128 and through a 10K resistor to the base of transistor 146. A 62K resistor is coupled between the base of transistor 146 and the positive terminal of bridge 128. The collector of transistor 146 is coupled through a relay coil 148 to the negative terminal of bridge 128. The normally-open relay switch 150 associated with relay coil 148 is coupled across resistor 120.

In operation, when switch 20 is in its center position, the instrument 10 is OFF. When switch 20 is in its position with contact made with terminal 92, or with terminal 98, power is supplied to both of bridges 78, 128. The voltage supplied to bridge 78 is rectified and appears across capacitor 80 and is regulated by the circuit including transistors 82, 84 and diode 86 and their associated circuitry. The voltage supplied to bridge 128 is rectified and appears across capacitor 130 and is regulated by resistor 132 and Zener diode 134. If switch 20 is in its illustrated position such that contact is made to terminal 92, +HVDC supply 96 provides a high-magnitude positive potential on output terminal 108. This potential is supplied through resistor 116 to probe plate 30. If the instrument 10 is placed such that probe plate 30 is located where there are negative ions, ions impact against plate 30, causing an ion current to flow through the neutral terminal 103 and resistor 120 to ground. When switch 20 is in its position in which contact is made to terminal 98, voltage supplied from regulator 82, 84, 86 and associated circuitry causes a high-magnitude negative potential to appear at terminal 112 of −HVDC supply 102. This high-magntiude negative potential is supplied through resistor 118 to plate 32. If the instrument 10 is placed in the vicinity of positive ions, ions impacting against plate 32 cause an ion current to flow through the neutral terminal 103 and resistor 120 to ground. In either case, a potential is generated across resistor 120 as the ion current flows. This potential is indicated by voltmeter 14, giving a direct readout of the ion current.

The shield 52 is coupled to the common terminal of the high voltage supplies 96, 102. This prevents any current from plates 30, 32 through the shield 52 from returning through resistor 120, thus eliminating any error signal. Since shield 52 can be no more than 200 millivolts from ground potential (the limit of meter 14), current from the shield 52 does not affect the voltage fields created by the supplies 96, 102 which drive the sensing plates 30, 32, respectively.

To avoid spurious readings on voltmeter 14 during energization of the circuit of FIG. 3, transistors 144, 146 and their associated circuitry are provided. Transistors 144, 146 and their associated components comprise a Schmitt trigger, the load of which is coil 148. Immediately after movement of switch 20 from its OFF position to either of its ON positions, transistor 146 is rendered conductive, causing current to flow in coil 148 and closing switch 150 to short resistor 120. Capacitor 140 begins to charge through resistor 138. After a predetermined time, the charging of capacitor 140 is sufficiently complete that the voltage on the base of transistor 144 drops sufficiently that transisor 144 is rendered conductive. Transistor 146 now is rendered non-conductive as a result of the conduction of transistor 144. This interrupts current flow through the coil 148, opening switch 150 and permitting the ion current-related voltage to appear across resistor 120 and be read by meter 14.

Figure 4:
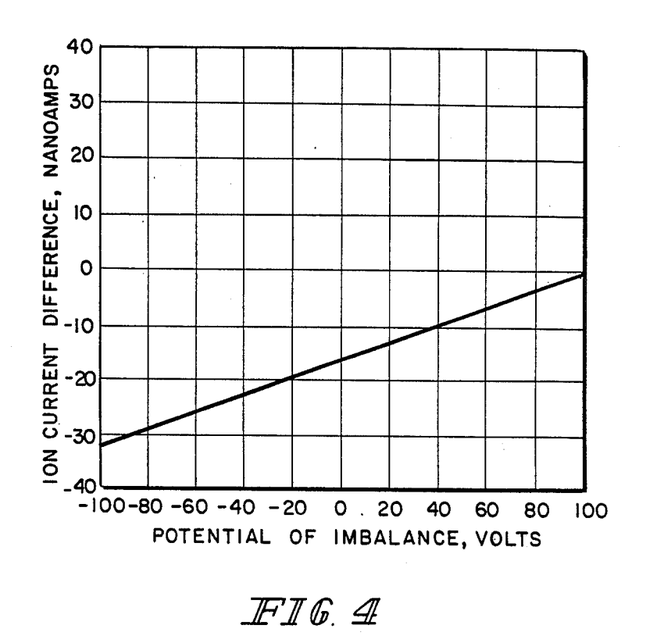
FIG. 4 is a graph of ion current differences, in nanoamperes versus potential of imbalance, in volts, for the ion current meter of FIGS. 1-3 under a first set of operating conditions.
Figure 5:
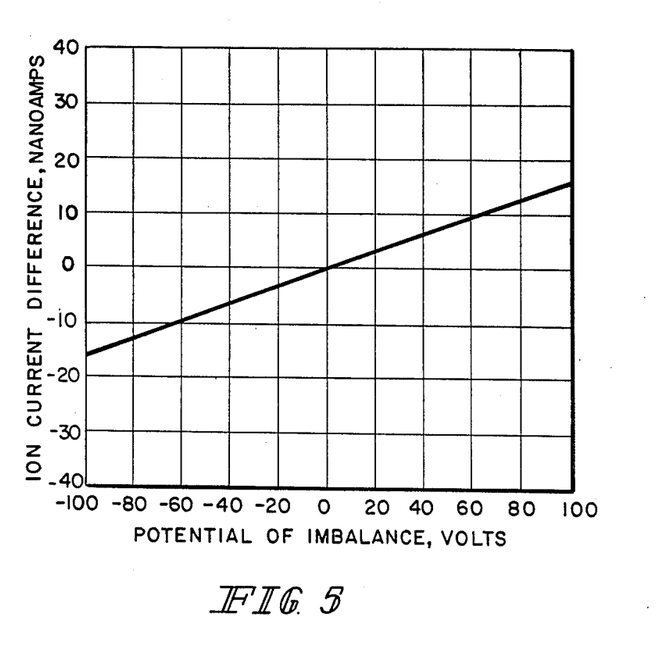
FIG. 5 is a graph of ion current difference, in nanoamperes, versus potential of imbalance, in volts, for the ion current meter of FIGS. 1-3 under a second set of operating conditions.

Referring now to FIGS. 4–5, ion flow imbalance is a very important characteristic of any air ionizer. The ideal ionizer should generate equal densities of positive and negative ions. If ions of one polarity predominate, ion flow imbalance is said to exist. This results in a net charge deposition on objects exposed to the ion flow from the ionizer. If an object exposed to the ion flow is conductive and grounded, the charge will bleed off to ground. If the object is a nonconductor or is otherwise isolated from ground, the net charge will accumulate on it, and the electrical potential of the object will rise. The magnitude of that potential will depend on the magnitude of the imbalance of ion flow. The conventional technique for determining an imbalance of ion flow involves measuring the potential which results on an object from exposure to such an imbalance. This is a complex procedure involving use of specialized instruments and procedures. A study was conducted with the instrument of the present invention, as described thus far. It was found that the instrument can be used to determine ion flow imbalance. The method for determining ion flow imbalance with the apparatus of the present invention involves comparison of positive and negative ionizing current readings. It was found that the difference between absolute values of positive and negative ionizing currents measured with the apparatus is a linear function of the potential of imbalance. After determining that function, the user of the instrument is able to determine potential of imbalance from the ionizing current readings. FIG. 4 shows the functional relationship for the apparatus of the present invention, with equal magnitude potentials (+5 kV and −5 kV) applied to sensing plates 30, 32, respectively.

It can be seen from FIG. 4 that zero potential of imbalance does not correspond to zero ion flow imbalance. It has been determined that measured negative current generally is higher than measured positive current. The greater mobility of negative ions appears to be a major contributing factor to this bias. Mobility of ions can be thought of as the ions' ability to move under the influence of an electric field. Therefore, when potentials on both plates 30, 32 of the instrument as described thus far are equal and equal numbers of positive and negative ions are present, more negative ions will be attracted to the positive plate 30 during negative current measurements than positive ions to the negative plate 32 during positive current measurements.

It is preferable, with a balanced ion flow, to read equal values of positive and negative currents. Under these conditions, the sign of the difference between positive and negative current will correspond to the polarity of predominating ions. To achieve this preferred result, the higher negative ion mobility must be compensated. One way to do this is by applying a somewhat lower magnitude potential to the positive plate 30 of the apparatus. It has been experimentally determined that one pair of plate potential values which provides the desired result is a positive plate 30 potential of +3.5 kV and a negative plate 32 potential of −5 kV. Potentiometer 162, 164 (FIG. 3) are provided to permit these types of potential magnitude adjustments at the plates 30, 32. The functional relationship which results under these operating conditions is illustrated in FIG. 5. Other potential magnitude pairs also can provide the desired result.

Another way to achieve this result would be to adjust the relative areas of the sensor plates, such as by increasing the negative plate 32 area and/or reducing the positive plate 30 area, to compensate for difference in ion mobility. Of course, a combination of these two techniques, relative area and potential adjustments, can also provide the desired compensation.

During the manufacturing process, or immediately after, air ionizers are typically tested, not only for efficiency, but also for ion generation balance. In a typical test set-up, an object, such as a conductive plate, is suspended so that no current will flow from it to ground or to it from ground, and the air ionizer under test is aimed at it and energized. The build-up of ions of one charge or the other on it is measured by an electrostatic voltmeter to prevent the voltage measurement from loading the plate. The ion imbalance in the emitted stream of ions can be determined using the instrument described in connection with FIGS. 1–3. The potential on the plate which results from this ion imbalance is directly read from the electrostatic voltmeter. The graphs of FIGS. 4–5 illustrate the functional relationship between this potential of imbalance and the ion current imbalance for a particular isolated object, such as a plate. In any object under test, these functional relationships can be established in this manner. Once the functional relationships are known, the potential of imbalance for the object can be determined by considering the graph of the functional relationship for that object and by knowing the ion current imbalance for the particular ionizer being used to charge that object.

What is claimed is:

1. An ion measuring apparatus comprising high-magnitude positive and negative potential sources, each of the high-magnitude potential sources having a high-magnitude potential output terminal, two electrodes for positioning adjacent the location of ions, the electrodes having areas for exposure to the ions, means for coupling the high-magnitude potential output terminal of each of the high-magnitude potential sources to a respective one of the electrodes, and means for selectively energizing one or the other of the electrodes from a respective one of the high-magnitude potential sources, the means for selectively energizing one or the other of the electrodes comprising supply for providing operating potential, each of the high-magnitude potential sources having an operating potential input terminal, a switch having a position in which operating potential is coupled to the operating potential input terminal of the high-magnitude positive potential supply and a position in which operating potential is coupled to the operating potential input terminal of the high-magnitude negative potential supply, each of the high-magnetide potential sources further comprising a neutral terminal, the instrument further comprising means for sensing current flows from the neutral terminals of the high-magnetic potential sources to references potential, the means for sensing current flows from the neutral terminals of the high-magnitude potential sources comprising a resistor, means for coupling the resistor in series between the neutral terminals of both high-magnitude potential sources and reference potential, a voltmeter, and means for coupling the voltmeter in parallel with the resistor.

2. The apparatus of claim 1 and further comprising a circuit for delaying the display by the voltmeter of voltage across the resistor.

3. The apparatus of claim 2 wherein the delay circuit comprises a relay including an energizing coil and switch for energization by the coil, means for coupling the relay switch in circuit with the resistor, means for timing an interval after energization of the instrument and means for coupling the timing means to the relay coil.

4. The apparatus of claim 3 wherein the timing means comprises a Schmitt trigger.

5. The apparatus of claim 1 wherein each electrode comprises a plate having an irregular edge, the irregular edges of the plates being complementarily configured for close spacing of the irregular edges from each other.

6. The apparatus of claim 5 where in the plates together comprise a somewhat rectangular array.

7. The apparatus of claim 6 wherein the irregular edges comprise multiple, finger-like protrusions, and the protrusions forming the irregular edge of one plate are interleaved with the protrusions forming the irregular edge of the other plate, defining between the irregular edges a non-conductive space.

8. The apparatus of claim 5 wherein the plates have substantially equal areas.

9. The apparatus of claim 1 and further comprising means defining a shield surrounding and closely spaced from the electrodes, and means for coupling the shield to the neutral terminals of the high-magnitude potential sources.

10. An ion measuring apparatus comprising a supply for providing operating potential, high-magnitude positive and negative potential sources, each of the high-magnitude potential sources having an operating poential input terminal, a high-magnitude potential output terminal and a neutral terminal, means for selectively coupling the operating potential input terminal of one or the other of the high-magnitude potential sources to the operating potential supply, means for coupling the netural terminals of the high-magnetide potential sources to each other, means for sensing current flows from the neutral terminals of the high-magnitude potential sources, two plates for positioning adjacent the location of ions, the plates having equal areas for exposure to the ions, and means for coupling the high-magnitude potential output terminal of each of the high-magnitude potential sources to a respective one of the plates, the means for sensing current flows from the neutral terminals of the high-magnitude potential sources comprising a resistor, means for coupling the resistor in series between the neutral terminals of both high-magnitude potential sources and ground, a voltmeter, and means for coupling the voltmeter in parallel with the resistor.

11. The apparatus of claim 10 and further comprising a circuit for delaying the display by the voltmeter of any voltage across the resistor.

12. The apparatus of claim 11 wherein the delay circuit comprises a relay including an energizing for coupling the relay switch in circuit with the resistor, means for timing an interval after energization of the instrument, and means for coupling the timing means to the relay coil.

13. The apparatus of claim 12 wherein the relay switch is open when no current flows in the relay coil, and the timing means comprises a Schmitt trigger.

14. The apparatus of claim 10 wherein each plate has an irregular edge, the irregular edges of the plates being complementarily configured for close spacing of the irregular edges from each other.

15. The apparatus of claim 14 wherein the irregular edges comprise multiple, finger-like protrusions and the protrusions forming the irregular edge of one plate are interleaved with the protrusions forming the irregular edge of the other plate, defining between the irregular edges a serpentine non-conductive space.

16. The apparatus of claim 10 and further comprising means defining a shield surrounding and closely spaced from the plates, and means for coupling the shield to the neutral terminals of the high-magnitude potential sources.

17. A method for measuring the ion flow imbalance of an ionizer comprising the steps of providing high magnitude positive and negative potential supplies, the magnitudes of which are independently selectively variable, providing two electrodes for positioning adjacent the flow of ions from the ionizer, the electrodes having areas for exposure to the ions, alternately energizing the electrodes from respective ones of the high magnitude potential supplies, alternately sensing ion flows to the respective electrodes, independently varying the magnitudes of the potentials supplied from the positive and negative supplies to their respective electrodes until the ion flows to the two electrodes are substantially equal, and comparing the magnitudes of the potentials.

18. The method of claim 17 wherein the step of providing two electrodes comprises the step of providing two plate-like electrodes having substantially equal areas, the step of alternately sensing ion flows to the respective electrodes comprises the step of exposing the substantially equal areas of the two electrodes to the ions, and the step of alternately energizing the electrodes from respective ones of the high magnitude potential supplies comprises the step of alternately energizing the supplies.

19. A method for measuring the ion flow imbalance of an ionizer comprising the steps of providing high magnitude positive and negative potential supplies, providing two electrodes, the geometries of which are independently selectively variable, for positioning adjacent the flow of ions from the ionizer, the electrodes having areas for exposure to the ions, alternately energizing the electrodes from respective ones of the supplies, alternately sensing ion flow to the respective electrodes, independently varying the geometries of the electrodes until the ion flows to the two electrodes are equal, and comparing the geometries of the electrodes.

20. The method of claim 19 wherein the step of providing two electrodes, the geometries of which are independently selectively variable comprises the step of providing more than two plate-like electrodes having different predetermined areas, and the step of independently varying the geometries of the electrodes comprises the step of substituting an electrode having a first predetermined area for another electrode having a second and different predetermined area.

21. The method of claim 20 whrein the step of providing high magnitude positive and negative potential supplies comprises the step of providing high magnitude positive and negative potential supplies, the magnitudes of which are independently selectively variable, independently varying the magnitudes of the potential supplies, and comparing the magnitudes of the potentials.

22. A method for determining ion flow imbalance comprising the steps of providing high-magnitude positive and negative potential sources, each having a high-magnitude potential output terminal, providing two electrodes for positioning adjacent the location of ions, the electrodes having areas for exposure to the ions, alternately enenrgizing one or the other of the two electrodes from respective high-magnitude potential sources and sensing the current flows to the electrodes as they are alternately energized, the step of alternately energizing one or the other of the two electrodes from respective high-magnitude potential sources comprising the steps of providing a supply of operating potential for the high-magnitude potential sources, and switching the supply of operating potential alternately between the high-magnitude potential sources, the step of sensing the current flows to the electrodes as they are alternately energized comprising the steps of providing neutral terminals on each of the high-magnitude potential sources and sensing current flows from the neutral terminals of the high-magnitude potential sources to reference potential.

23. The method of claim 22 wherein the step of sensing current flows from the neutral terminals of the high-magnitude potential sources to reference potential comprises the steps of providing a resistor, coupling the resistor in series between the neutral terminals of the high-magnitude potential sources and reference potential, and sensing a voltage developed across the resistor by current flow through the resistor between the neutral terminals of the high-magnitude potential sources and reference potential.

24. A method for determining the ability of an object subjected to an unbalanced stream of positive and negative ions to sustain a potential difference from a reference potential comprising the steps of establishing a functional relationship between an unbalance between positive and negative ion flows on the one hand and potential difference between the object and a reference potential on the other hand, measuring the positive ion current in the stream, measuring the negative ion current in the stream, determining the unbalance, and determining from the unbalance and the functional relationship the ability of the object to sustain the potential difference.

25. The method of claim 24 wherein the steps of measuring the positive ion current in the stream, measuring the negative ion current in the stream, and determining the unbalance together comprise the steps of providing high-magnitude positive and negative potential sources, each having a high-magnitude potential output terminal, providing two electrodes for positioning adjacent the stream of positive and negative ions, the electrodes having areas for exposure to the ions, alternately energizing the electrodes from respective high-magnitude potential sources, and alternately sensing the ion current flows to the electrodes.

26. The method of claim 24 wherein the steps of measuring the positive ion current in the stream, measuring the negative ion current in the stream, and determining the unbalance together comprise the steps of providing high-magnitude positive and negative potential sources, the magnitudes of which are independently selectively variable, each high-magnitude potential source having a high-magnitude potential output terminal, providing two electrodes for positioning adjacent the stream of positive and negative ions, the electrodes having areas for exposure to the ions, alternately energizing the electrodes from respective high-magnitude potential sources, independently varying the magnitudes of the potentials supplied from the positive and negative supplies to their respective electrodes until the ion flows to the two electrodes are substantially equal, and comparing the magnitudes of the potentials.

27. The method of claim 24 wherein the steps of measuring the postive ion current in the stream, measuring the negative ion current in the stream, and determining the unbalance together comprise the steps of providing high-magnitude positive and negative potential supplies, providing two electrodes, the geometries of which are independently selectively variable for positioning adjacent the stream of positive and negative ions, the electrodes having areas for exposure to the ions, alternately energizing the electrodes from respective ones of the supplies, alternately sensing ion flow to the respective electrodes, independently varying the geometries of the electrodes until the ion flows to the two electrodes are equal, and comparing the geometries of the electrodes.

* * * * *

UNITED STATES PATENT AND TRADEMARK OFFICE
CERTIFICATE OF CORRECTION

PATENT NO. : 4,774,472

DATED : September 27, 1988

INVENTOR(S) : Mark Blitshteyn and William S. Wright

It is certified that error appears in the above-identified patent and that said Letters Patent is hereby corrected as shown below:

At column 9, line 41, please delete "high-magnetic" and insert therefor --high-magnitude--;

At column 9, line 65, please delete "where in" and insert therefor --wherein--;

At column 10, lines 15-16, please delete "poential" and insert therefor --potential--;

At column 10, line 40, after the word "energizing" please insert --coil and a switch for energization by the coil, means--; and At column 11, line 41, please delete "whrein" and insert therefor --wherein--.

Signed and Sealed this

Twenty-first Day of February, 1989

*Attest:*

DONALD J. QUIGG

*Attesting Officer*      *Commissioner of Patents and Trademarks*